US010883080B2

(12) United States Patent
Shimizu et al.

(10) Patent No.: US 10,883,080 B2
(45) Date of Patent: Jan. 5, 2021

(54) METHOD FOR CULTURING ANIMAL CELL COMPOSITION, METHOD FOR PRODUCING ANIMAL CELL COMPOSITION USING SAME, AND ANIMAL CELL COMPOSITION

(71) Applicant: Tokyo Women's Medical University, Tokyo (JP)

(72) Inventors: Tatsuya Shimizu, Tokyo (JP); Yuji Haraguchi, Tokyo (JP); Yuki Kagawa, Tokyo (JP); Katsuhisa Sakaguchi, Tokyo (JP)

(73) Assignee: TOKYO WOMEN'S MEDICAL UNIVERSITY, Tokyo (JP)

( * ) Notice: Subject to any disclaimer, the term of this patent is extended or adjusted under 35 U.S.C. 154(b) by 180 days.

(21) Appl. No.: 15/736,035

(22) PCT Filed: Jun. 24, 2016

(86) PCT No.: PCT/JP2016/068906
§ 371 (c)(1),
(2) Date: Dec. 13, 2017

(87) PCT Pub. No.: WO2016/208747
PCT Pub. Date: Dec. 29, 2016

(65) Prior Publication Data

US 2018/0155673 A1 Jun. 7, 2018

(30) Foreign Application Priority Data

Jun. 25, 2015 (JP) ................................ 2015-127783

(51) Int. Cl.

| | |
|---|---|
| ***C12N 1/12*** | (2006.01) |
| ***C12N 5/077*** | (2010.01) |
| ***A61L 27/36*** | (2006.01) |
| ***A61L 27/38*** | (2006.01) |

(52) U.S. Cl.
CPC ............ *C12N 1/12* (2013.01); *A61L 27/3604* (2013.01); *A61L 27/3895* (2013.01); *C12N 5/0657* (2013.01); *C12N 5/0658* (2013.01); *C12N 2502/70* (2013.01); *C12N 2529/10* (2013.01); *C12N 2533/90* (2013.01)

(58) Field of Classification Search
None
See application file for complete search history.

(56) References Cited

U.S. PATENT DOCUMENTS

| | | | | |
|---|---|---|---|---|
| 2005/0136092 | A1* | 6/2005 | Rotem | A61F 2/022 424/423 |
| 2010/0312165 | A1* | 12/2010 | Stern | C12M 21/02 604/19 |
| 2013/0173018 | A1* | 7/2013 | Sakaguchi | C12M 21/08 623/23.72 |
| 2016/0310547 | A1* | 10/2016 | Cohen | A61K 35/748 |

FOREIGN PATENT DOCUMENTS

WO 2011/116936 A1 9/2011

OTHER PUBLICATIONS

Zijffers et al., "Maximum Photosynthetic Yield of Green Microalgae in Photobioreactors", Mar Biotechnol., 2010, vol. 12, pp. 708-718. (Year: 2010).*
Haraguchi et al, "Thicker three-dimensional tissue from a "symbiotic recycling system" combining mammalian cells and algae", Scientific Reports, Jan. 31, 2017, vol. 7, No. 1, 10 pages.
Sakaguchi et al, "Construction of three-dimensional vascularized cardiac tissue with cell sheet engineering", Journal of Controlled Release, May 1, 2015, vol. 205, pp. 83-88.
Schenck et al, "Photosynthetic biomaterials: A pathway towards autotrophic tissue engineering", Acta Biomaterialia, Mar. 1, 2015, vol. 15, pp. 39-47.
Hopfner et al., "Development of photosynthetic biomaterials for in vitro tissue," Acta Biomaterialia, 2014, vol. 10, No. 6, pp. 2712-2717 (fig. 4-6).
Lode et al., "Green bioprinting: Fabrication of photosynthetic algae-laden hydrogel scaffolds for biotechnological and medical applications," Eng. Life Sci., Mar. 2015, vol. 15, No. 2, pp. 177-183.
International Application No. PCT/JP2016/068906, International Search Report dated Sep. 27, 2016, 1 page.

* cited by examiner

*Primary Examiner* — Laura Schuberg
(74) *Attorney, Agent, or Firm* — Kilpatrick Townsend & Stockton LLP

(57) ABSTRACT

An object of the present invention is to obtain a thicker animal cell composition by a simple and less expensive method. Namely, an object of the present invention is to provide a method for culturing a thicker animal cell composition by eliminating the hypoxia associated with animal cell compositions, a method for producing an animal cell composition containing unicellular algae, and an animal cell composition.

The present invention provides a method for culturing an animal cell composition in a culture medium in the presence of unicellular algae and under exposure to light. According to the method of the present invention, oxygen can be continuously supplied in the culture medium, cell damage is alleviated, and a thicker cell composition can be obtained in the absence of a capillary network.

8 Claims, 13 Drawing Sheets

C2C12 cell sheet

C2C12 cell sheet + algae

Creatine Kinase

<10-Layered>

(A) (B)

METHOD FOR CULTURING ANIMAL CELL COMPOSITION, METHOD FOR PRODUCING ANIMAL CELL COMPOSITION USING SAME, AND ANIMAL CELL COMPOSITION

CROSS-REFERENCE TO RELATED APPLICATIONS

This application is a 371 National Phase Application of PCT/JP2016/068906, filed Jun. 24, 2016, which application claims priority to Japanese Application no. 2015-127783, filed Jun. 25, 2015, the disclosures all of which are incorporated herein by reference.

TECHNICAL FIELD

The present invention relates to a method for culturing an animal cell composition. In addition, the present invention relates to a method for producing an animal cell composition using that method for culturing an animal cell composition, and an animal cell composition. Furthermore, the present application claims priority on the basis of Japanese Patent Application No. 2015-127783, filed with the Japan Patent Office on Jun. 25, 2015, the entire contents of which are incorporated herein by reference.

BACKGROUND ART

The development of therapeutic technologies using cells has become increasingly active in recent years, and the clinical application thereof is being attempted at numerous institutions both at home and abroad. Various methods have been developed for this purpose, such as a method consisting of harvesting cells from the body of a patient, culturing the cells outside the body and then retransplanting the cells into the body of the patient, a method consisting of introducing a specific gene into isolated cells followed by returning the cells to the body, and a method consisting of seeding cells on a scaffold to three-dimensionally construct tissue for transplantation. These methods are used in the form of medical technologies in the field of regenerative medicine, and have the potential of enabling treatment of diseases for which a complete cure has conventionally been difficult. It is hoped that radical therapeutic technologies using cells will be developed for practical use in the future that can be applied to numerous patients.

Conventional therapy using cells employed a method consisting of suspending cells proliferated by culturing in vitro in a suitable solution followed by transplanting into the body by injection or infusion. However, many of the transplanted cells failed to remain at the transplanted site, with nearly all of the cells leaving the affected area, thereby frequently resulting in limited therapeutic efficacy. Cell culture dishes having a polymer, which demonstrates an upper limit or lower limit critical solution temperature of 0° C. to 80° C. with respect to water, coated onto the surface of the culture substrate (temperature-responsive culture dishes) have been developed for the purpose of solving this problem (Patent Document 1). After having cultured cells using these culture dishes at a temperature lower than the upper limit critical solution temperature or higher than the lower limit critical solution temperature of the polymer coated on the surface of the culture dishes followed by culturing the cells to confluency, the cells can be recovered non-invasively in the form of a cell sheet by bringing to a temperature higher than the upper limit critical solution temperature or lower than the lower limit critical solution temperature. In the past, proteases such as trypsin or dispase were required to be used to recover adherent cells from culture dishes, and these proteases ended up decomposing matrix proteins expressed on the cell surface along with proteins composing the gap junctions used to connect cells. Since proteins required to adhere cells in this manner ended up being decomposed, cells were recovered in a dispersed state, and as a result thereof, made it difficult for the cells to take to tissue in the case of transplant. On the other hand, cell sheets obtained using temperature-responsive culture dishes have the superior characteristic not found in the prior art of enabling cells to rapidly become established at an affected area due to the presence of adhesive protein since proteins on the cell surface are subjected to hardly any damage. As a result, the effects of cell transplant can be maximized, thereby dramatically contributing to the advancement of cell transplantation technology. This type of technology is referred to as cell sheet engineering, and efforts are currently being made towards the development and practical application of novel therapeutic technologies for curing diseases of the skin, cornea, heart, esophagus, knee cartilage or periodontal tissue and the like through the application of this technology.

Although the establishment of cell sheet engineering has resulted in dramatic changes in the area of cell therapy technology, organ transplant remains to be the most effective therapeutic approach for critically ill patients for which cell transplant is considered unlikely to demonstrate a therapeutic effect. However, the number of available organs is overwhelmingly small in comparison with the number of patients requiring organ transplant, thus resulting in the need for the development of a technology capable of constructing and supplying organs or tissue. Cell sheet engineering technology can also be applied to solve this problem as well, and attempts are being made to construct thick body tissue by layering cell sheets (Patent Document 2). In the case of conventionally transplanting cells in the form of a cell sheet, although it was only possible to transplant a number of cells proportional to the area of the cell sheet, the development of technology that enables a plurality of cell sheets to be layered to accumulate the cells three-dimensionally has made it possible to transplant a larger number of cells. However, in the case of layering four or more layers of cell sheets, nutrients and oxygen in the culture medium are unable to penetrate to the interior of the layered cell sheets, thereby resulting in the problem of necrosis of interior cells. In order to solve this problem, methods have been developed consisting of producing a thicker tissue by layering cell sheets within the body of an animal and constructing vascular networks within the cell sheets for supplying oxygen (Non-Patent Document 1), and laminating cell sheets on a vascular bed in vitro (Patent Documents 3 and 4). The construction of a capillary network within a cell sheet enables oxygen, which is unable to reach cells inside the layered cell sheets by the diffusion of dissolved oxygen alone, to reach those cells, thereby making it possible to construct thicker tissue.

PRIOR ART DOCUMENTS

Patent Documents

[Patent Document 1] Japanese Unexamined Patent Publication No. H02-211865

[Patent Document 2] International Publication No. WO 02/008387

[Patent Document 3] International Publication No. WO 12/036224

[Patent Document 4] International Publication No. WO 12/036225

Non-Patent Documents

[Non-Patent Document 1] Shimizu, T., et al., Polysurgery of cell sheet grafts overcomes diffusion limits to produce thick, vascularized myocardial tissues, FASEB. J., 20(6), 708-710 (2006)

DISCLOSURE OF THE INVENTION

Problems to be Solved by the Invention

Methods consisting of layering a cell sheet within the body of an animal as described above had the problem of requiring the transplant site to be repeatedly opened daily, thereby placing an excessive burden on the recipient. In addition, methods using a vascular bed had the problem of excessive complexity of the device used to perfuse the culture medium, thereby resulting in the need for the development of a simpler and less expensive culture method. An object of the present invention is to obtain a thicker animal cell composition by a simple and less expensive method that solves the aforementioned problems. Namely, an object of the present invention is to provide a method for culturing a thicker animal cell composition by eliminating the hypoxia associated with animal cell compositions, a method for producing an animal cell composition containing unicellular algae, and an animal cell composition.

Means for Solving the Problems

The inventors of the present invention conducted research and development in addition to studies from various perspectives in order to solve the aforementioned problems. As a result, the inventors of the present invention surprisingly found that animal cells can be cultured in the presence of unicellular algae without being damaged. In addition, it was also found that unicellular algae have the ability to carry out photosynthesis even under conditions of co-cultivating with animal cells, thereby making it possible to obtain cell compositions having greater thickness in comparison with that found in the prior art both easily and less expensively due to the action of enzymes produced by the unicellular algae. Namely, the present invention is as described below.

[1] A method for culturing an animal cell composition in a culture medium in the presence of unicellular algae and under exposure to light.

[2] The method described in [1], wherein the animal cell composition contains two or more cell layers.

[3] The method described in [2], wherein the cell layers comprise a cell sheet.

[4] The method described in [3], wherein the cell sheet is a cell sheet composed of four or more layers.

[5] The method described in any of [1] to [4], wherein the unicellular algae include green algae, unicellular blue-green algae, unicellular red algae, unicellular axle algae and/or unicellular algae of the class Ulvophyceae.

[6] The method described in any of [1] to [5], wherein the unicellular algae include *Chlorococcum littorale, Acaryochloris marina, Cyanidium caldarium, Galdieria partita, Stichococcus sp.* and/or filamentous ulvophytes.

[7] The method described in any of [1] to [6], wherein the animal cell composition contains mammalian cells.

[8] The method described in any of [1] to [7], wherein the animal cell composition contains cardiomyocytes or myoblasts.

[9] The method described in any of [1] to [8], wherein the cell medium includes culture medium for culturing mammalian cells.

[10] The method described in any of [2] to [9], wherein at least a portion of the unicellular algae are seeded between two or more cell layers.

[11] A method for producing an animal cell composition containing unicellular algae by culturing an animal cell composition in a culture medium in the presence of unicellular algae and under exposure to light.

[12] An animal cell composition containing animal cells and unicellular algae.

[13] The animal cell composition described in [12], wherein the animal cell composition is obtained by layering two or more cell layers.

[14] The animal cell composition described in [13], wherein at least a portion of the unicellular algae is interposed between the two or more cell layers.

[15] The animal cell composition described in any of [12] to [14], wherein the unicellular algae include *Chlorococcum littorale, Acaryochloris marina, Cyanidium caldarium, Galdieria partita, Stichococcus sp.* and/or filamentous ulvophytes.

Effects of the Invention

According to the method of the present invention, the concentration of oxygen dissolved in a culture medium can be enhanced, enabling oxygen to be continuously supplied to a cell composition that became hypoxic in the case of conventional methods. In addition, increases in the ammonia concentration in a culture medium can be inhibited. As a result, cell damage can be alleviated and a thicker cell composition can be obtained in the absence of a capillary network.

BRIEF DESCRIPTION OF THE DRAWINGS

FIG. 2(A) shows a system used in the present invention. FIG. 2(B) is a graph indicating oxygen concentration versus the height from the bottom of a culture dish used to culture unicellular algae.

FIG. 3(A) is graph in which oxygen concentration is plotted against the height from the bottom of a culture dish in the absence of *Chlorococcum littorale*, while FIG. 3(B) is a graph of that in the presence of *Chlorococcum littorale*. FIG. 3(C) is a graph indicating the oxygen consumption rate (OCR) of a monolayer C2C12 cell sheet in the presence or absence of *Chlorococcum littorale* and in the presence or absence of exposure to light. FIG. 3(D) is a graph indicating the OCR of a monolayer cardiomyocyte sheet in the presence or absence of *Chlorococcum littorale* and in the presence or absence of exposure to light.

BEST MODE FOR CARRYING OUT THE INVENTION

Figure 1:
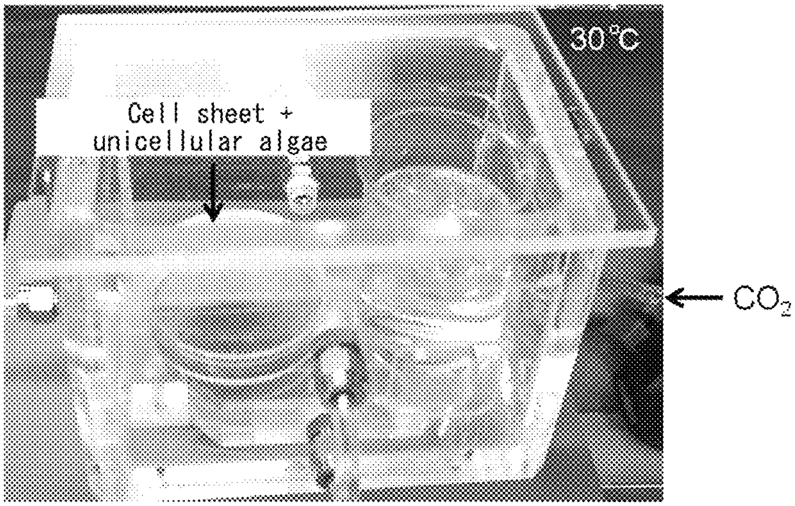
FIG. 1 is a drawing showing a culturing apparatus used in the method for culturing cells that uses a cell sheet and unicellular algae of the present invention.

The present invention relates to a method for culturing an animal cell composition, a method for producing an animal cell composition that uses that culture method, and an animal cell composition produced according to that method. In the present invention, an animal cell composition includes any composition containing animal cells. For example, the animal cell composition may be a composition composed of a mixture of cells and collagen, proteoglycan, laminin, laminin 5, fibronectin, hyaluronic acid, entactin, tenascin or elastin that composes the extracellular matrix, or a composition containing cells and an extracellular matrix produced by cells. In addition, protein that composes the extracellular matrix may be gene recombinant protein or protein produced from cells incorporating a gene that encodes that protein or cells introduced with a gene through the use of a vector and the like. In addition, the form of the animal cell composition may be a form obtained by layering a plurality of layered cells, or that obtained by suspending cells in a gel containing an extracellular matrix and pouring into a mold. In addition, the animal cell composition may also contain unicellular algae to be subsequently described, although not limited thereto.

Although there are no particular limitations on the origin of the animal species of the cells used in the present invention, examples thereof include mammals such as humans, rats, mice, guinea pigs, marmosets, rabbits, dogs, cats, sheep, pigs, goats, monkeys, chimpanzees and immunodeficient variations thereof, as well as birds, reptiles, amphibians, fish and insects. Cells derived from humans are preferably used in the case of using the cell composition of the present invention to treat a human, cells derived from pigs are preferably used to treat a pig, cells derived from monkeys are preferably used to treat a monkey, and cells derived from chimpanzees are preferably used to treat a chimpanzee. In addition, in the case the subject undergoing treatment is a human, the cells used may be cells harvested from the patient per se (autologous cells), cells harvested from the cells of another person (heterologous cells), or commercially available cells.

The cell type, number of cells and proportions of cells used in the present invention may be suitably selected or adjusted corresponding to the tissue, organ, or site of the body used for transplant or an evaluation model, or application thereof, and so forth. For example, in the case of using for the purpose of serving as a method for regenerating myocardial tissue or evaluating myocardial function, examples of cells used in the present invention include any one type, or mixtures of two or more types, of cardiomyocytes, cardiac myoblast, myoblasts, mesenchymal stem cells, vascular endothelial cells, vascular endothelial progenitor cells, fibroblasts, bone marrow-derived cells and fat-derived cells, and there are no restrictions whatsoever on the type thereof. In the case of using for the purpose of serving as a method for regenerating liver tissue, creating an artificial liver mimicking liver tissue, or evaluating the function of liver tissue, examples of cells used in the present invention include any one type, or mixtures of two or more types, of hepatocyte, sinusoidal endothelial cells, Kupffer cells, stellate cells, pit cells, biliary epithelial cells, vascular endothelial cells, vascular endothelial progenitor cells, fibroblasts, bone marrow-derived cells, fat-derived cells and mesenchymal stem cells, and there are no restrictions whatsoever on the type thereof. In the case of using for the purpose of serving as a method for regenerating kidney tissue, creating an artificial kidney mimicking kidney tissue, or evaluating kidney function, examples of cells used in the present invention include any one type, or mixtures of two or more types, of renal cells, granule cells, collecting duct epithelial cells, parietal epithelial cells, podocytes, mesangial cells, smooth muscle cells, renal tubular cells, intercalated cells, glomerular cells, vascular endothelial cells, vascular endothelial progenitor cells, fibroblasts, bone marrow-derived cells, fat-derived cells and mesenchymal stem cells, and there are no restrictions whatsoever on the type thereof. In the case of using for the purpose of serving as a method for regenerating adrenal tissue, creating an artificial adrenal gland mimicking the adrenal glands, or evaluating adrenal function, examples of cells used in the present invention include any one type, or mixtures of two or more types, of adrenomedullary cells, adrenocortical cells, glomerulosa cells, fasciculata cells, reticular layer cells, vascular endothelial cells, vascular endothelial progenitor cells, fibroblasts, bone marrow-derived cells, fat-derived cells and mesenchymal stem cells, and there are no restrictions whatsoever on the type thereof. In the case of using for the purpose of serving as a method for regenerating skin or evaluating skin function, examples of cells used in the present invention include any one type, or mixtures of two or more types, of epidermal keratinocytes, melanocytes, pilomotor cells, hair follicle cells, vascular endothelial cells, vascular endothelial progenitor cells, fibroblasts, bone marrow-derived cells, fat-derived cells and mesenchymal stem cells, and there are no restrictions whatsoever on the type thereof. In the case of using the for the purpose of serving as a method for regenerating mucosal tissue or evaluating the function of mucosal tissue, cells harvested from tissue that composes a mucous membrane, for example, are used for the cells used in the present invention. Examples of types of mucous membranes include the buccal mucosa, gastric mucosa, intestinal mucosa, olfactory epithelium, oral mucosa and uterine mucosa. Examples of cells harvested from mucosal tissue include any one type of cell and mixtures of two or more types of cells, and there are no restrictions whatsoever on the type thereof. In addition, these cells may be, but are not limited to, cells induced to differentiate from ES cells, iPS cells, Muse cells or mesenchymal stem cells.

In the present invention, cells obtained by mincing body tissue can be used for the cells that compose the cell composition. In this case, numerous types of cells are present in the cells derived from body tissue. For example, in an example of the present invention, although a cell sheet is fabricated by mincing rat cardiac tissue and using cardiomyocytes contained therein, the resulting cell sheet contains not only cardiomyocytes, but also fibroblasts, parietal cells and vascular endothelial cells derived from the cardiac tissue, and unnecessary cells can be removed using a cell sorter or antibody, or conversely required cells can be added, according to the specific purpose. A "cardiac cell sheet" as referred to in the present description contains not only the aforementioned cardiomyocytes, but also such cells as fibroblasts, parietal cells, and vascular endothelial cells.

The cell sheet of the present invention is one aspect of a cell composition, and refers to a group of cells composed of one or a plurality of sheet-like cell layers obtained by culturing cells in a cell culture vessel followed by detaching the cells from the cell culture vessel. Although there are no particular limitations thereon, examples of methods used to obtain a cell sheet include a method consisting of detaching cells in the form of a sheet from the surface of a cell culture vessel while maintaining an adhered state between cells by culturing cells in a cell culture vessel coated with a polymer for which the molecular structure thereof changes due to stimulation by such factors as temperature, pH or light, and then altering the surface of the cell culture vessel by changing temperature, pH or light, and a method consisting of culturing cells in an arbitrary cell culture vessel and physically detaching the cells from the edges of the cell culture vessel using a tweezers and the like. A particularly preferable method consists of culturing cells on a cell culture support having a polymer coated on the surface thereof, which undergoes a change in hydration force over a temperature range of 0° C. to 80° C., within a temperature range for which the hydration force of the polymer is weak, followed by culturing the cells and then detaching the cells in the form of a sheet by changing the temperature of the culture medium to a temperature at which the hydration force of the polymer is strong. At that time, the cells are cultured on a cell culture support having a polymer coated on the surface thereof, which undergoes a change in hydration force over a temperature range of 0° C. to 80° C., over a temperature range for which the dehydration force of the polymer is weak. That temperature is preferably the temperature at which cells are cultured, and is normally in the vicinity of 37° C. The temperature-responsive polymer used in the present invention may be a homopolymer or copolymer. An example of such a polymer is described in Japanese Unexamined Patent Publication No. H2-211865.

It may be difficult to adhere cells to the cell culture vessel depending on the type of cell, and in such cases, culturing may be carried out by coating the cell culture vessel with, for example, collagen, laminin, laminin 5, fibronectin or Matrigel either alone or as a mixture of two or more types thereof. Coating the cell culture vessel with these cell adhesion proteins may be carried out in accordance with ordinary methods, and for example, the cell culture vessel is normally coated by applying an aqueous solution of a cell adhesion protein to the surface of the culture vessel followed by rinsing to remove the aqueous solution.

In the method of the present invention, although varying according to the animal species and cell type of the cells used, the number of cells seeded to fabricate one aspect of a cell layer in the form of a cell sheet is typically $0.4\times10^6$ to $10\times10^6$ cells/cm$^2$, preferably $0.5\times10^6$ to $8\times10^6$ cells/cm$^2$, and more preferably $0.25\times10^6$ to $5\times10^6$ cells/cm$^2$. In the present invention, when detaching and recovering a cultured cell sheet from a temperature-responsive culture vessel, the cell sheet can be detached by making the temperature of the culture vessel having the cultured cells adhered thereto to be a temperature equal to or higher than the upper limit critical solution temperature or equal to or lower than the lower limit critical solution temperature of the coated polymer. At that time, detachment of the cells may be carried out in the culture medium or in another isotonic solution, and which of these is used can be selected according to the specific objective. Methods consisting of gently tapping the culture vessel, shaking the culture vessel, stirring the culture medium using a pipette or using a tweezers can be used either alone or in combination for the purpose of detaching and recovering the cells more rapidly and efficiently. Culturing conditions other than temperature are in accordance with ordinary methods, and there are no particular limitations thereon. For example, the culture medium used may be a culture medium containing a known serum such as fetal bovine serum (FBS), or a serum-free culture medium to which such serum has not been added.

The following provides an explanation of the above matters using the example of poly(N-isopropylacrylamide) for the temperature-responsive polymer. Poly(N-isopropylacrylamide) is known to be a polymer having a lower limit critical solution temperature of 31° C., and when in the free state, demonstrates aggregation of the polymer chain and clouding as a result of undergoing dehydration in water at a temperature of 31° C. or higher. Conversely, at a temperature of 31° C. or lower, the polymer chain is hydrated and becomes soluble in water. In the present invention, this polymer is coated and immobilized on the surface of a Petri dish or other culture vessel. Thus, if the temperature is 31° C. or higher, although the polymer on the surface of the culture vessel dehydrates in the same manner, since the polymer chain is coated and immobilized on the surface of the culture vessel, the surface of the culture vessel demonstrates hydrophobicity. Conversely, if the temperature is 31° C. or lower, although the polymer on the surface of the culture vessel is hydrated, since the polymer chain is coated and immobilized on the surface of the culture vessel, the surface of the culture vessel demonstrates hydrophilicity. The hydrophobic surface at this time is suitable for cell adhesion and proliferation, while the hydrophilic surface is prevents cell adhesion, thereby enabling cells during culturing or a cell sheet to be detached simply by cooling.

There are no particular limitations on the form of the cell culture vessel used to fabricate a cell sheet used in the present invention, and examples thereof include dishes, multiplates, flasks, cell inserts for culturing on a porous membrane and flat films. In the case the cultured cells are epithelial cells, the use of a cell insert enables the culture medium to make contact above and below the cells, which is preferable in terms of layering the cells. Examples of cell culture vessels undergoing coating include glass, modified glass and compounds such as polystyrene or polymethyl methacrylate normally used to culture cells, as well as substances routinely able to be used to impart a shape, such as polymer compounds or ceramics other than those described above.

One aspect of a cell layer of the present invention in the form of a cell sheet is not susceptible to damage by proteases represented by dispase or trypsin during culturing. Consequently, the cell sheet detached from the cell culture vessel retains adhesion proteins, thereby enabling the desmosome structure between cells to be maintained when cells are detached in the form of a sheet. As a result thereof, in the case of affixing the cell sheet to an affected part of the body or layering the cell sheet, the cell layer is able to adhere thereto and efficiently be engrafted to tissue. Although a typical example of a protease in the form of dispase is known to allow cells to be detached while retaining 10% to 40% of the desmosome structure between cells, since basement membrane-like proteins present between cells and the culture vessel end up being nearly completely destroyed, the resulting cell sheet has low strength. In contrast, the cell sheet of the present invention allows 60% or more of desmosome structures and basement membrane-like proteins to remain intact, thereby making it possible to obtain the various effects previously described.

There are no particular limitations on the method used to fabricate a cell composition having a plurality of cell layers in the present invention, and examples thereof include a method consisting of seeding cells in a cell culture vessel and coating a gel containing protein that composes the extracellular matrix (such as laminin, collagen, gelatin, cadherin, hyaluronic acid, fibronectin, fibrin, elastin, chitin, chitosan or hydronectin) thereon, followed by seeding and layering the cells to obtain a cell composition having cell layers, and a method consisting of detaching cultured cells in the form of sheets and layering the cultured cell sheets using a cultured cell transfer tool as necessary. There are no particular limitations on the temperature of the culture medium at that time provided the temperature thereof is equal to or lower than the upper limit critical solution temperature of the polymer coated on the surface of the culture vessel in the case the polymer has such a temperature, and provided that the temperature thereof is equal to or higher than the lower limit critical solution temperature of the polymer coated on the surface of the culture vessel in the case the polymer has such a temperature. However, it goes without saying that culturing at a low temperature so as to prevent proliferation of the cultured cells (for example, 10° C. or lower) or at a high temperature so as to cause cell death of the cultured cells (for example, 50° C. or higher) is unsuitable. There are no particular limitations on culturing conditions other than temperature, and are only required to be in accordance with ordinary methods. For example, the culture medium used may be a culture medium containing a known serum such as fetal bovine serum (FBS) or a serum-free culture medium to which such serum has not been added. In addition, a tool for transferring the cell sheets may be used as necessary. Although there are no particular limitations on the material or form of the tool provided it is able to grasp and hold detached cell sheets, examples of the materials thereof normally include materials such as polyvinylidene fluoride (PVDF), silicon, polyvinyl alcohol, urethane, cellulose and derivatives thereof, chitin, chitosan, collagen, gelatin or fibrin gel, and is used in the form of a film, porous membrane, nonwoven fabric or woven fabric that contacts the cell sheet.

The algae used in the present invention is the generic term for those living organisms that produce oxygen by photosynthesis excluding mosses, ferns and seed plants that primarily thrive above ground. Algae are capable of proliferating while producing oxygen and nutrients on their own provided they are placed in an environment required for photosynthesis. In the present invention, oxygen concentration in a culture medium is increased by oxygen produced by algae photosynthesis, and this oxygen is then supplied directly or indirectly to an animal cell composition. In addition, in the present invention, since algae have the ability to fix a metabolite of animal cells in the form of ammonia, the algae are able to inhibit increases in the concentration of ammonia, which is harmful to the culturing of animal cells. Algae fulfill the role of supplying oxygen to the animal cell composition either directly or indirectly during the course of culturing, and since the algae also fulfill the role of inhibiting increases in ammonia concentration, unicellular algae that can be suspension cultured in a culture medium are preferable. In the present invention, "unicellular algae" refer to individual algae composed of a single cell, and include unicellular algae that form colonies resulting from the gathering of a plurality of individual unicellular algae. Examples of unicellular algae include green algae, which use chlorophyll a and b for the primary pigments of chloroplasts, unicellular blue-green algae (cyanobacteria), which use chlorophyll d for the primary pigment of chloroplasts, and unicellular red algae, which use chlorophyll d and phycobiliprotein for the primary pigments of chloroplasts. Specific examples include green algae in the form of *Chlamydomonas reinhardtii* of the class Chlorophyceae, order Chlamydomonas, *Dunaliella salina* of the order Dunaliella, *Volvox carteri* of the order Volvocales, *Chlorococcum littorale* of the order Chlorococcales, *Hydrodictyon reticulatum, Pediastrum duplex* and *Scenedesmus dimorphous* of the order Sphaeropleales, *Chlorella vulgaris* of the class Trebouxiophyceae, order Chlorellales, and *Euglena gracilis* and *Euglena proximia* of the phylum Euglenophyta, class Euglenophyceae, order Euglenida. Examples of unicellular blue-green algae include *Acaryochloris marina* of the phylum Cyanobacteria. Examples of unicellular red algae include *Cyanidium caldarium* of the phylum Rhodophyta, class Cyanidiophyceae, order Cyanidiales and *Galdieria partita* of the phylum Rhodophyta, class Cyanidiophyceae, order Cyanidiales. Examples of unicellular axle algae include *Stichococcus sp.* of the phylum Chlorophyta, class Charophyceae, order Klebsormidiales. In addition, other examples of algae used in the present invention include filamentous ulvophytes, which are unicellular algae of the class Ulvophyceae. The unicellular algae used in the present invention may also be genetic recombinants obtained by genetic modification of the examples of unicellular algae listed above.

The unicellular algae used in the present invention can preferably be cultured in a culture medium for animal cells. In addition, the temperature during culturing is suitably selected according to the type of animal cells used and type of unicellular algae. A temperature is selected that enables both animal cells and unicellular algae to thrive while also allowing photosynthesis by the unicellular algae. Examples of temperature ranges at which culturing can be carried out include a range of 19° C. to 50° C., 20° C. to 49° C., 21° C. to 48° C., 22° C. to 47° C., 23° C. to 46° C., 24° C. to 45° C., 25° C. to 44° C., 26° C. to 43° C., 27° C. to 42° C., 28° C. to 41° C. and 29° C. to 40° C.

The culture medium for culturing mammalian cells used in the present invention can be suitably selected according to the animal species and cell type, and there are no particular limitations thereon. In addition, there are also no particular limitations on the culture medium for culturing unicellular algae prior to co-cultivating with mammalian cells, and is suitably selected in accordance with established methods corresponding to the type of unicellular algae. The culture medium may be refluxed using a bioreactor and the like or may be stirred in a culture tank equipped with a stirrer, and is suitably selected according to the type of unicellular algae, animal species of the animal cells, and properties of the cell type.

There are no particular limitations on the light exposure method used in the present invention, and for example, a commercially available fluorescent lamp, LED or incandescent light bulb can be used. The selection of a suitable light source corresponding to the absorption spectrum of the photosynthetic pigment possessed by the unicellular algae used makes it possible to maximally enhance photosynthesis efficiency. For example, algae are exposed to light from a light source of a wavelength in the vicinity of 400 nm to 450 nm and 650 nm to 700 nm in the case of unicellular algae having chlorophyll a, light from a light source of a wavelength in the vicinity of 450 nm to 480 nm and 630 nm to 670 nm in the case of unicellular algae having chlorophyll b, light from a light source of a wavelength in the vicinity of 700 nm to 750 nm in the case of unicellular algae having chlorophyll d, or light from a light source of a wavelength in the vicinity of 500 nm to 650 nm in the case of unicellular algae having phycobiliprotein. In the case of using unicellular algae having multiple types of chlorophyll and/or phycobiliprotein, the unicellular algae are exposed to a light source that combines the aforementioned wavelengths.

In the present invention, co-cultivation of unicellular algae and mammalian cells may be carried out by culturing in a state in which the unicellular algae are suspended in a culture medium, culturing by suspending the mammalian cells and unicellular algae followed by seeding in a culture dish, culturing in a state in which the unicellular algae are seeded between cell layers and interposed between the cell layers, or culturing using a combination of these methods. A method that combines a plurality of the aforementioned methods is preferable for obtaining a thicker cell composition obtained by layering four or more layers of cell sheets.

Although the number of cells of the unicellular algae at the start of culturing is suitably adjusted according to the type of unicellular algae and type of animal cells, examples thereof include $0.1\times10^7$ to $10\times10^7$, $0.15\times10^7$ to $9.5\times10^7$, $0.2\times10^7$ to $9\times10^7$, $0.25\times10^7$ to $8.5\times10^7$, $0.3\times10^7$ to $8\times10^7$ and $0.35\times10^7$ to $7.5\times10^7$ unicellular algae cells per 1 mL of culture medium.

In the present description, the terms "aerobic respiration" and "anaerobic respiration" refer to the same terms as those known among persons with ordinary skill in the art. In general, "aerobic respiration" refers to a catabolic metabolic system that enables eukaryotic cells having mitochondria to utilize oxygen. "Aerobic respiration" refers to that composed of three metabolic systems broadly categorized as the glycolytic system, citric acid cycle and oxidative phosphorylation, and sugars are broken down into carbon dioxide and water by going through these metabolic systems. ATP is produced as a result of going through this process. In the case of aerobic respiration, oxygen is required in the oxidative phosphorylation process, and for example, approximately 30 moles of ATP are produced as a result of one mole of glucose going through the aforementioned three metabolic systems under conditions in which sufficient oxygen is present. On the other hand, under conditions in which sufficient oxygen is not present, the aforementioned oxidative phosphorylation reaction is unable to proceed, and the respiration that occurs at this time is generally referred to as "anaerobic respiration". Anaerobic respiration goes through a glycolytic system in the same manner as aerobic respiration. As a result, two moles of lactate are produced from one mole of glucose after going through two moles of pyruvic acid, and two moles of ATP are produced in this process. Thus, from the viewpoint of ATP production output, aerobic respiration can be said to be superior in terms of energy efficiency. Moreover, the lactate produced during anaerobic respiration is known to impart cytotoxicity, and a culturing method that suppresses production of lactate is therefore preferable.

In the present description, the ratio of "aerobic respiration" and "anaerobic respiration" can be predicted from the ratio of the amount of lactate produced to the amount of glucose consumed in the culture medium (L/G ratio). In the case all respiration was tentatively assumed to be in the form of anaerobic respiration, since one mole of glucose are converted to two moles of lactate, the L/G ratio approaches two. Conversely, in the case of aerobic respiration, since there is no lactate produced, the L/G ratio approaches zero. Namely, a change in the L/G ratio makes it possible to predict a change in the ratios of aerobic respiration and anaerobic respiration.

According to the present invention, although animal cell compositions are thought to undergo necrosis due to a shortage of oxygen in the case of conventional culturing methods, when cultured in the presence of unicellular algae, a thicker animal cell composition can be obtained without causing necrosis by, for example, co-cultivating the animal cell composition with unicellular algae.

EXAMPLES

Although the following provides a more detailed explanation of the present invention based on examples thereof, these examples do not in any way limit the present invention.

(Cells Used, Culture Method and Fabrication of Cell Sheet)

C2C12 mouse myoblasts (Sumitomo Dainippon Pharma Co., Ltd., Osaka, Japan) were cultured in Dulbecco's modified Eagle's medium (DMEM, Sigma-Aldrich, Inc., St. Louis, U.S.A.). C2C12 cell sheets were prepared using temperature-responsive culture dishes (UpCell®, CellSeed Inc., Tokyo, Japan) according to the method of Y. Haraguchi, et al. (Y. Haraguchi, et al., Fabrication of functional three-dimensional tissues by stacking cell sheets in vitro, Nat. Protoc. 7 (2012), 850-858, and Y. Haraguchi, et al., Development of a new assay system for evaluating the permeability of various substances through three-dimensional tissue, Tissue Eng., Part C, Methods 16 (2010), 685-692).

Neonatal rat cardiac cells were isolated from the ventricles of one-day-old Sprague-Dawley (SD) rats (CLEA Japan Inc., Tokyo, Japan) and cultured in a culture medium for culturing mammalian cells (trade name: Tissue Perfusion Culture Medium, Kohjin Bio Co., Ltd., Saitama, Japan). Cardiac cell sheets and layered cell sheets were prepared using temperature-responsive culture dishes (UpCell®, CellSeed Inc., Tokyo, Japan) according to the method of Y. Haraguchi, et al. (Y. Haraguchi, et al., Fabrication of functional three-dimensional tissues by stacking cell sheets in vitro, Nat. Protoc. 7 (2012), 850-858), the method of H. Sekine, et al. (H. Sekine, et al., In vitro fabrication of functional three-dimensional tissues with perfusable blood vessels, Nat. Commun. 4 (2013), 1399), and the method of K. Sakaguchi, et al. (K. Sakaguchi, et al., In vitro engineering of vascularized tissue surrogates, Sci. Rep. 3 (2013), 1316).

(Culturing of Unicellular Algae)

The unicellular algae, *Chlorococcum littorale*, was purchased from the Biological Research Center of the National Institute of Technology and Evaluation (Tokyo, Japan), and cultured at room temperature (approx. 27° C. to 28° C.) while continuously exposing to a light source (approx. 500 lux to 700 lux) using Daigo's IMK medium (Wako Pure Chemical Industries, Ltd., Tokyo, Japan) and artificial seawater (trade name: Daigo's Artificial Seawater SP, Nihon Pharmaceutical Co., Ltd.). The unicellular algae ($2.5\times10^7$ cells) were cultured for 0 days or 1 day under temperature conditions of 30° C. while continuously exposing to a light source (1313±45 lux (n=3)) in 35 mm polystyrene culture dishes (Becton, Dickinson & Co., Franklin Lakes, N.J., U.S.A.) using culture medium for culturing mammalian cells and Daigo's IMK medium (Table 1) followed by measuring the amount of oxygen produced with an oxygen concentration measurement system to be subsequently described. Illuminance was measured with an illuminometer (As One Corp., Tokyo, Japan).

pipette to recover the rat cardiac cell sheet within the pipette. Culture medium containing unicellular algae and the cardiac cell sheet was discharged into a 60 mm polystyrene culture dish (Becton, Dickinson & Co., Franklin Lakes, N.J., U.S.A.) followed by again aspirating the culture medium with the same pipette so as not to aspirate the cardiac cell sheet.

A cardiac cell sheet detached from the temperature-responsive culture dish was again recovered in the aforementioned culture medium containing unicellular algae, and the culture medium containing the cardiac cell sheet and unicellular algae was discharged into the polystyrene culture dish containing the first cardiac cell sheet. At this time, the second cardiac cell sheet was laid on top of the first cell sheet. The aforementioned procedure was repeated to prepare five-layered and ten-layered cardiac cell sheets. The culture liquid containing unicellular algae used to prepare the cell sheets was used as is in subsequent culturing. As a result, a layered cell sheet was obtained in which unicellular algae were contained between cell sheets. A layered cell sheet not containing unicellular algae was prepared using the same procedure with the exception of excluding unicellular algae from the culture medium used in the aforementioned procedure.

(Co-Cultivation of Cell Sheets and Unicellular Algae)

Co-cultivation of mammalian cell sheets and algae was carried out under the conditions shown in Table 1. Cell sheet tissues consisting of a single layer or multiple layers were cultured in an acrylic culture box under conditions of 30° C., humidified atmosphere, 5% $CO_2$ and continuous exposure to light (1313±45 lux (n=3)) (FIG. 1). The culture medium was replaced every 24 hours and the culture medium recovered after culturing was used to measure metabolic activity and cell viability.

TABLE 1

Figure 2:
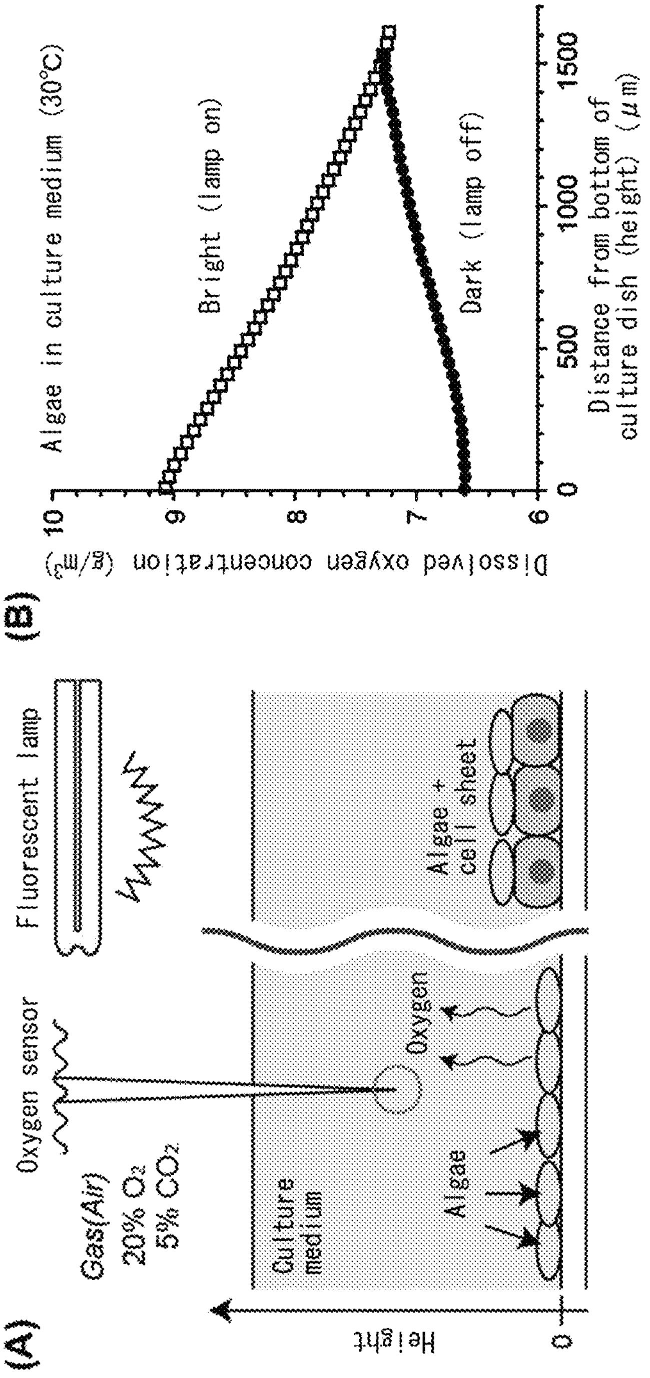
FIG. 2 is a drawing showing a system for measuring oxygen produced by *Chlorococcum littorale*.
Figure 3:
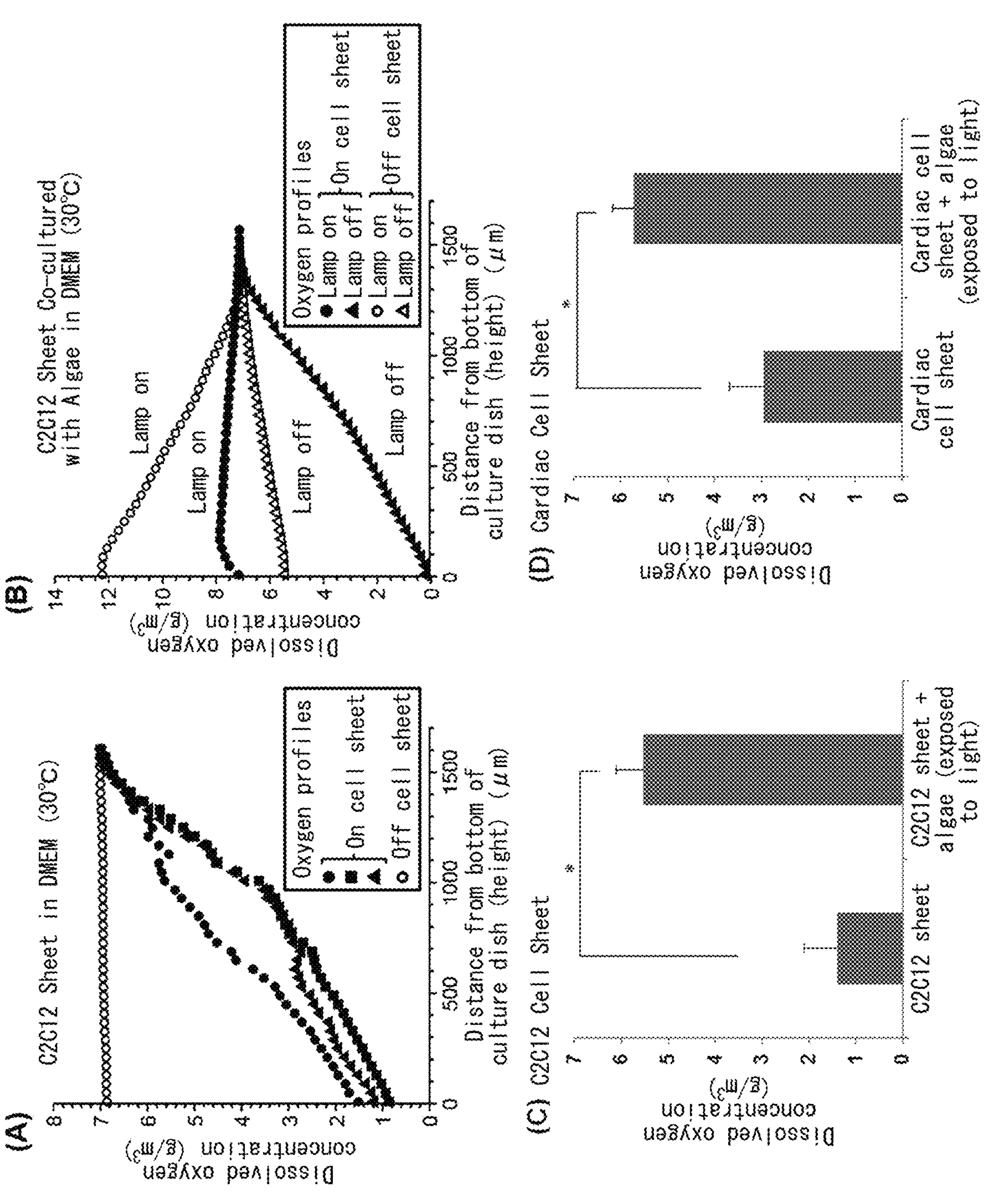
FIG. 3 is a drawing showing the oxygen concentration resulting from culturing a monolayer C2C12 cell sheet and a monolayer rat cardiomyocyte cell sheet in the presence or absence of *Chlorococcum littorale*.

| Drawing | Cells | No. of Unicellular Algae | No. of Cell Sheet Layers | Culture Medium | Amount of Culture Medium | Culture Temperature |
|---|---|---|---|---|---|---|
| FIG. 2 | *Chlorococcum littorale* | $2.5\times10^7$ | (—) | Culture medium for culturing mammalian cells | 2 mL | 30° C. |
| FIGS. 3A, 3B, 3C, 4, 5A, 5B, 6 | C2C12 cell sheet + *Chlorococcum littorale* | $2.5\times10^7$ | Monolayer | Dulbecco's modified Eagle's medium (DMEM) | 6 mL | 30° C. |
| FIG. 3D | Rat cardiac cell sheet + *Chlorococcum littorale* | $2.5\times10^7$ | Monolayer | Culture medium for culturing mammalian cells | 6 mL | 30° C. |
| FIGS. 7, 8, 9, 10, 11, 12, 13 | Rat cardiac cell sheet + *Chlorococcum littorale* | $2.5\times10^8$ | 5 layers, 10 layers | Culture medium for culturing mammalian cells | 6 mL | 30° C. |

(Preparation of Layered Cell Sheets Containing Unicellular Algae)

Monolayer rat cardiac cell sheets were prepared according to the previously described method. Culture medium was removed from the temperature-responsive culture dishes used to prepare rat cardiac cell sheets followed by the addition of 6 mL of culture medium for culturing mammalian cells containing $2.5\times10^7$ unicellular *Chlorococcum littorale* cells and aspirating all of the culture medium with a (Biochemical Assay and Cell Viability Assay)

Metabolic activity of cell sheet tissue was monitored by measuring the amount of glucose consumed and the amount of lactate produced in the culture medium. The release of lactate dehydrogenase (LDH) from the cells or the release of creatine kinase (CK) from muscle cells, including cardiac cells, was used as a common indicator of cell damage and cell viability. Glucose concentration was measured using the hexokinase UV method, lactate concentration was measured using the lactic oxidase method, LDH activity was measured using an LDH assay kit (Sicaliquid LDH J, Kanto Chemical Co., Inc., Tokyo, Japan), and CK activity was measured by enzymatic analysis according to the method of Y. Haraguchi, et al., (Y. Haraguchi, et al., Development of a new assay system for evaluating the permeability of various substances through three-dimensional tissue, Tissue Eng. Part C, Methods 16 (2010), 685-692), the method of W. Sekine, et al. (W. Sekine, et al., Thickness limitation and cell viability of multi-layered cell sheets and overcoming the diffusion limit by a porous-membrane culture insert, J. Biochip. Tissue Chip S2 (2011) 001), and the method of T. Shioyama, et al. (T. Shioyama, et al., New isolation system for collecting living cells from tissue, J. Biosci. Bioeng. 115 (2013), 100-103). In addition, ammonia concentration in the culture medium was determined by using the outsourcing service of a testing firm (SRL, Tokyo, Japan) using a calorimetric method.

(Measurement of Oxygen Concentration in Culture Medium)

The inventors of the present invention have recently developed an oxygen concentration measurement system that uses an oxygen microelectrode sensor (glass Clark-type oxygen microsensor having a tip measuring 8 μm to 12 μm in diameter (OX-10, Unisense A/S, Denmark) and a high-precision electronic balance (HTR-220, Shinko Denshi Co., Ltd., Japan). This apparatus constitutes a system capable of measuring the oxygen concentration at the location of the tip of an oxygen sensor from the bottom of a culture dish (FIG. 2A) (reference: Sekine, K., et al., Oxygen consumption of human heart cells in monolayer culture, Biochem. Biophys. Res. Commun., 2014; 452: 834-839). Oxygen concentration was measured in a humidified atmosphere containing 20% oxygen and 5% $CO_2$ in a glove box hypoxia workstation (Invivo$_2$ 300, Ruskinn Technology Ltd.). The oxygen concentrations and oxygen consumption rates (OCRs) of the cultured cells were evaluated in the presence (1103±25 lux (n=2)) or absence of a light source. Measurements were made at three locations in the culture dish followed by calculation of the average value thereof (reference: K. Sekine, et al., Oxygen consumption of human heart cells in monolayer culture, Biochem. Biophys. Res. Commun., 452 (2014), 834-839, and Y. Kagawa, et al., Direct measurement of local dissolved oxygen concentration spatial profiles in a cell culture environment, Biotechnol. Bioeng. 2015, June; 112(6): 1263-1274).

(Histological Analysis)

After culturing for 1 to 3 days, mono- or multi-layered cell sheets were fixed with 4% paraformaldehyde solution (Muto Pure Chemicals Co., Ltd., Tokyo, Japan). The fixed specimens were embedded in paraffin followed by preparing tissue sections and staining the sections with hematoxylin-eosin stain. In addition, the prepared specimens were stained using rabbit polyclonal anti-HIF-1α antibody using an outsourcing service (Kyodo Byori Inc., Kobe, Japan). The prepared tissues were observed with an optical microscope (Eclipse E800, Nikon Corp., Tokyo, Japan). The images were processed with an imaging system (NIS-Elements, Nikon Corp., Tokyo, Japan).

(Data Analysis)

All data was represented as the mean±standard deviation (SD). The unpaired Student t-test was used to compare two groups. A p value of less than 0.05 was considered to constitute a significant difference.

Example 1

(Detection of Oxygen Production from Unicellular Algae)

The unicellular algae, *Chlorococcum littorale*, was confirmed as to whether it can be cultured in culture medium for mammalian cells and whether or not it is able to produce oxygen by photosynthesis (FIG. 2). Saturated oxygen concentration was defined as the oxygen concentration in the vicinity of the surface of the culture medium that contacts the gaseous phase (oxygen concentration of the region farthest from the bottom of the culture dish in FIG. 2B: approx. 7.4 g/m$^3$). In the same manner as when using culture medium for algae, the unicellular algae were clearly determined to be able to produce oxygen by photosynthesis in excess of the saturated concentration even in the case of having cultured using culture medium for culturing mammalian cells, and were able to be cultured even when using culture medium for mammalian cells.

Example 2

(Co-Cultivation of Mammalian Cells and Unicellular Algae)

Cell sheets and unicellular algae were co-cultivated using mammalian cells (Table 1). Although the oxygen concentration of culture medium near the bottom of culture dishes in which C2C12 cell sheets were not present demonstrated a saturated state, oxygen concentration of culture medium at the bottom of culture dishes in which C2C12 cell sheets were present (left side of FIG. 2A) had decreased to a level approaching zero (FIG. 3A), thus demonstrating that the cell sheets are actively consuming oxygen. Oxygen concentration in the area where only unicellular algae are present and exposed to light was higher than the saturated oxygen concentration (FIG. 3B). Oxygen concentration of culture medium in the area where cell sheets and unicellular algae were both present and exposed to light (right side of FIG. 2A) was at the saturation level. On the basis thereof, mammalian cells and unicellular algae were determined to be able to be co-cultivated, and the unicellular algae were determined to retain the ability to sufficiently produce oxygen even when co-cultivated in this manner.

In the case of co-cultivating unicellular algae and cell sheets without exposing to light, the oxygen concentration of the culture medium decreased to a greater degree than in the case of the cell sheets alone (FIGS. 3B and 3C), thereby suggesting that the metabolism of the unicellular algae switched from photosynthesis to respiration. Consequently, oxygen consumption in the case of co-cultivation without exposing to light is thought to be greater than oxygen consumption in the case of culturing mammalian cells alone. A similar tendency was observed in the case of co-cultivating unicellular algae and rat cardiac cell sheets (FIG. 3D). The ability to produce and supply oxygen by unicellular algae was indicated to be able to be controlled by only the presence or absence of exposure to light.

Figure 4:
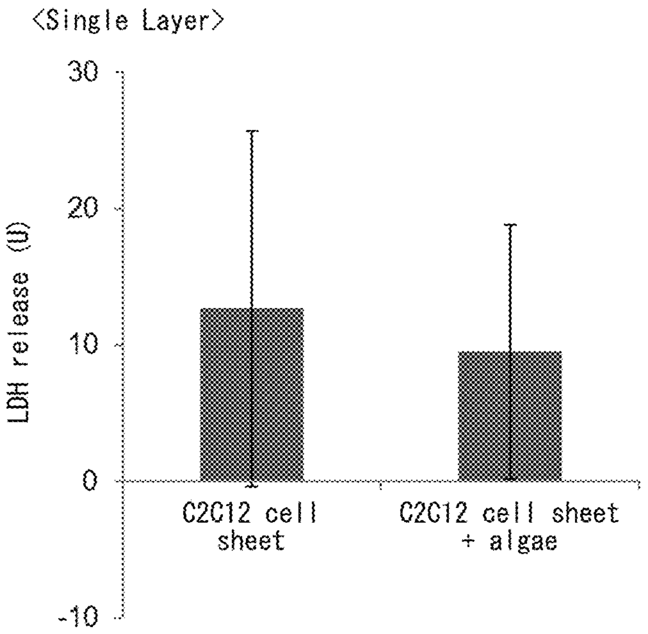
FIG. 4 is a graph indicating a comparison of the amounts of lactate dehydrogenase (LDH) released by a monolayer C2C12 cell sheet in the presence or absence of *Chlorococcum littorale.*
Figure 5:
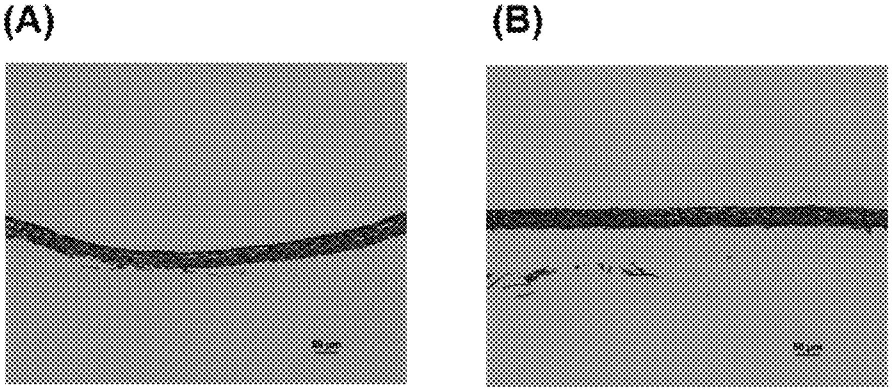
FIG. 5 depicts drawings showing the results of histological observation of a monolayer C2C12 cell sheet in the presence or absence of *Chlorococcum littorale.*

Co-cultivation with unicellular algae was investigated for the effect it has on mammalian cells. There were no significant differences in LDH release, which is used as an indicator of cell damage, regardless of the presence or absence of unicellular algae (FIG. 4). In addition, histological analysis did not reveal any morphological changes in any of the cell sheets regardless of the presence or absence of unicellular algae (FIGS. 5A and 5B). These results suggest that unicellular algae do not cause damage to mammalian cells even during co-cultivation of unicellular algae and mammalian cells.

Figure 6:
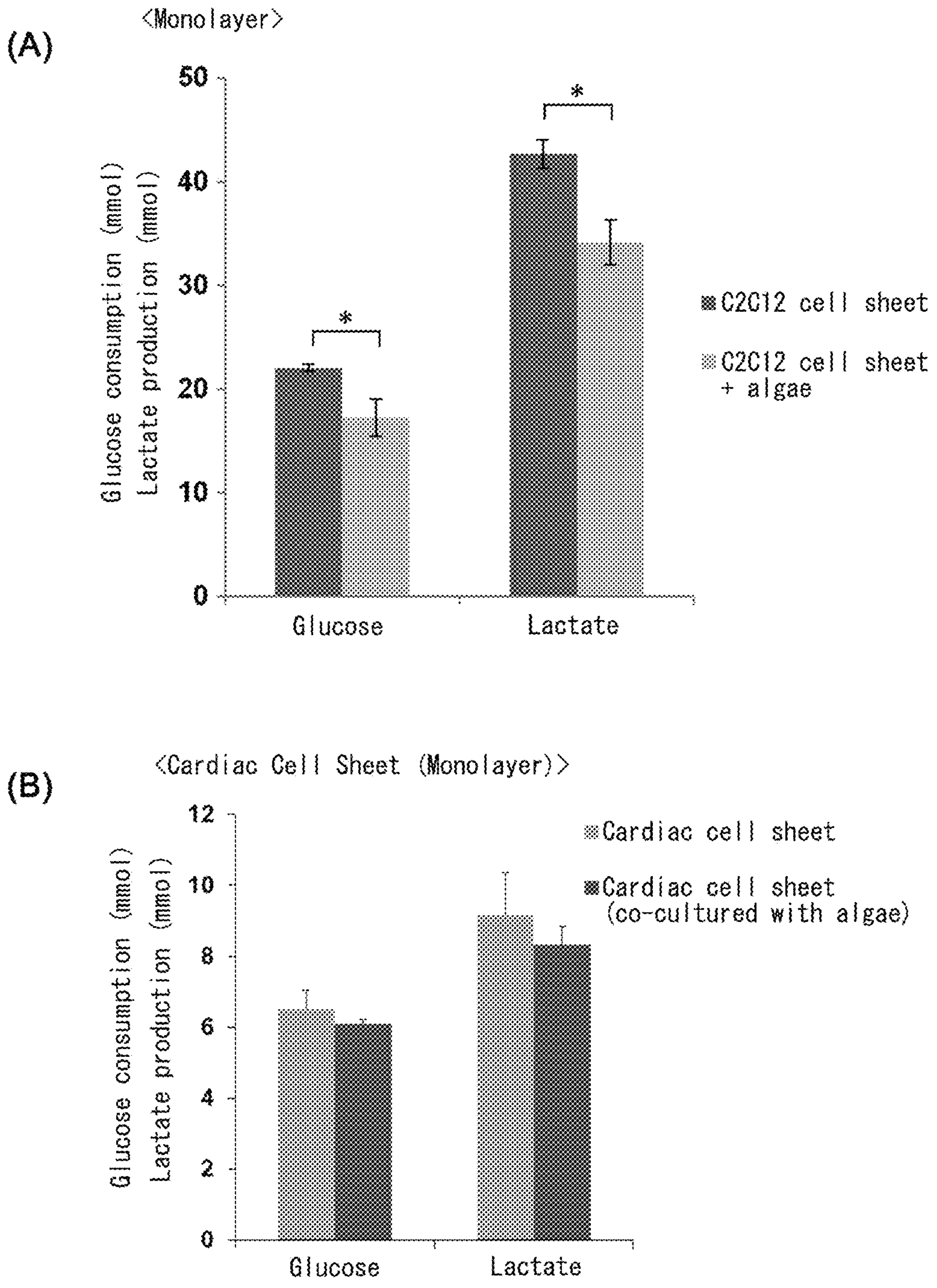
FIG. 6 depicts a graph indicating the amounts of glucose consumed and lactate produced by a monolayer C2C12 sheet (A) or a cardiomyocyte sheet (monolayer) (B) in the presence or absence of *Chlorococcum littorale.*

An investigation of the metabolism of the cell sheets revealed that both glucose consumption and lactate production decreased by 20% in the case of co-cultivation of unicellular algae and C2C12 cell sheets in comparison with culturing of the cell sheets alone (FIG. 6). C2C12 cells have been reported to demonstrate significant increases in glucose uptake and lactate production under hypoxic conditions as compared with normoxic conditions (W. Li, et al., Response of C2C12 myoblasts to hypoxia: The relative roles of glucose and oxygen in adaptive cellular metabolism, Biomed. Res. Int. 2013 (2013), 326-346). Reductions in glucose consumption and lactate production attributable to co-cultivation with unicellular algae are presumed to be the result of a transition from a hypoxic state to a normoxic state induced by the supply of oxygen from the unicellular algae.

Example 3

(Co-Cultivation of Unicellular Algae and Rat Cardiac Cells)

Figure 7:
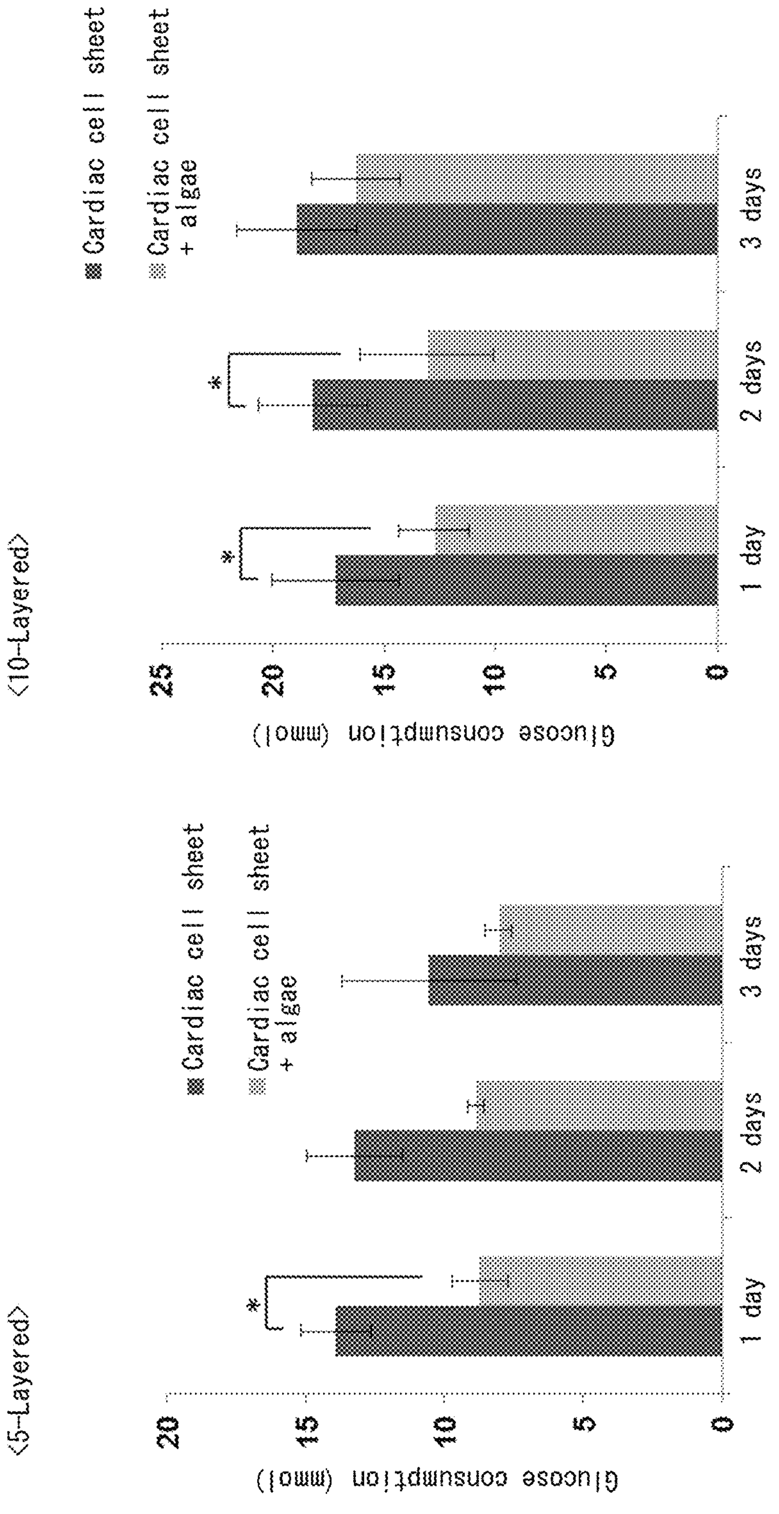
FIG. 7 depicts graphs indicating the amount of glucose consumed by a five-layered or ten-layered cardiomyocyte sheet in the presence or absence of *Chlorococcum littorale*. The amounts of glucose consumed in the culture supernatants were measured 1 day, 2 days and 3 days after the start of culturing.
Figure 8:
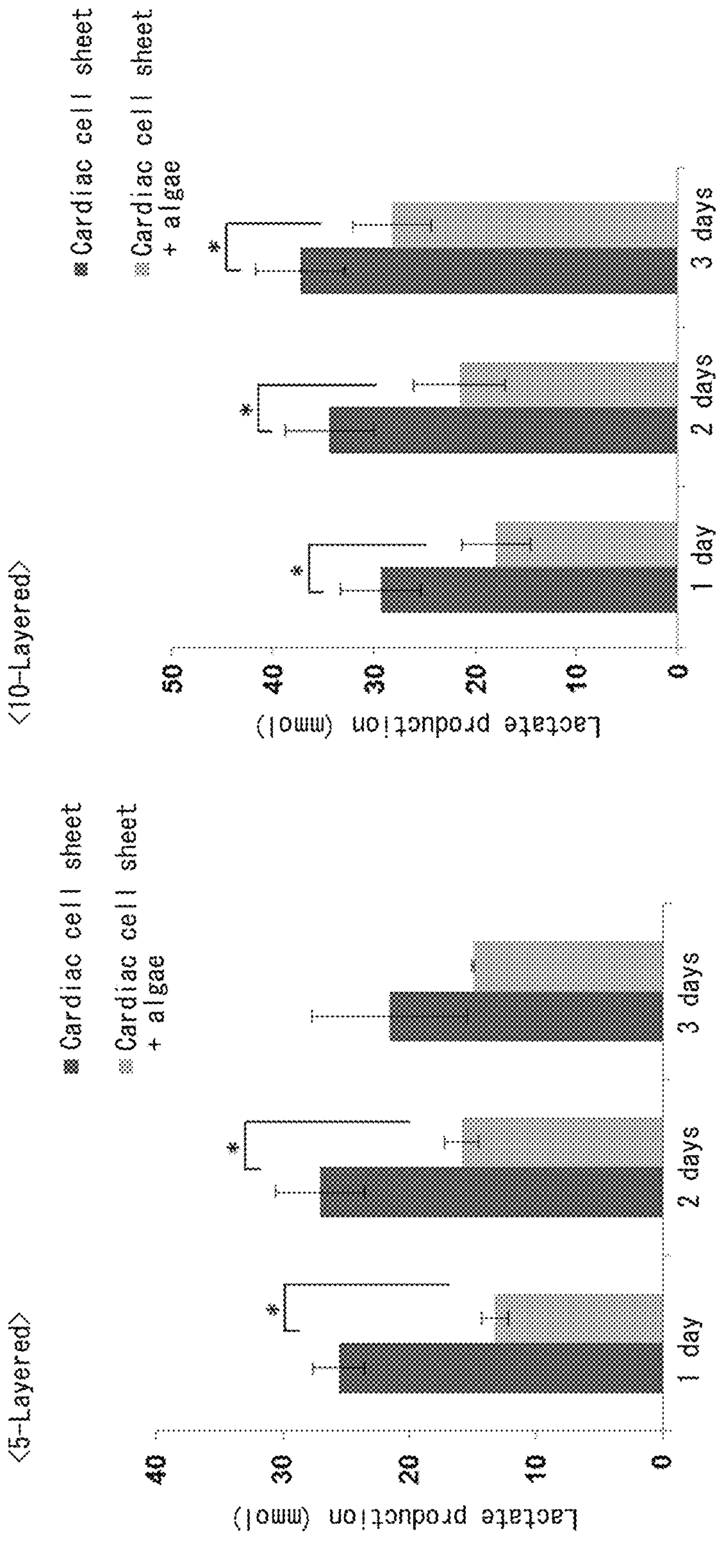
FIG. 8 depicts graphs indicating the amount of lactate produced by a five-layered or ten-layered cardiomyocyte sheet in the presence or absence of *Chlorococcum littorale*. The amounts of lactate produced in the culture supernatants were measured 1 day, 2 days and 3 days after the start of culturing.

Five-layered or 10-layered cell sheets were prepared under conditions of containing or not containing unicellular algae in order to fabricate thicker myocardial tissue. The 5-layered or 10-layered cardiac cell sheets containing unicellular algae demonstrated significant decreases in glucose consumption and lactate production in comparison with tissue obtained by culturing the cell sheets alone (FIGS. 7 and 8).

The ratio of lactate production to glucose consumption (L/G ratio) of the cells was used as an indicator in order to investigate whether the cells were engaged in aerobic respiration or anaerobic respiration. During anaerobic respiration, the L/G ratio is 2 in the case all pyruvate, which is the final metabolite of glucose metabolism, is converted to lactate. On the other hand, during aerobic respiration, a portion of the pyruvate is taken up into mitochondria and is completely oxidized by the tricarboxylic acid (TCA) cycle, thereby causing the L/G ratio to become smaller than 2. The results for L/G ratio in the present example are shown in Table 2.

TABLE 2

| Cell Type | Lactate/Glucose Ratio (L/G) (mol/mol) | | |
|---|---|---|---|
| | After 1 day of culturing | After 2 days of culturing | After 3 days of culturing |
| C2C12 cell sheets (1 layer) | 1.94 | NT | NT |
| C2C12 cell sheets (1 layer) + eukaryotic algae | 1.98 | NT | NT |
| Cardiac cell sheets (1 layer) | 1.4 | NT | NT |
| Cardiac cell sheets (1 layer ) + eukaryotic algae | 1.36 | NT | NT |
| Cardiac cell sheets (5 layers) | 1.84 | 2.05 | 2.04 |
| Cardiac cell sheets (5 layers) + eukaryotic algae | 1.52 | 1.79 | 1.86 |
| Cardiac cell sheets (10 layers) | 1.70 | 1.89 | 1.97 |
| Cardiac cell sheets (10 layers) + eukaryotic algae | 1.41 | 1.65 | 1.74 |

NT: Not tested

Measurement of the L/G ratio of the 5-layered and 10-layered cardiac cell sheets not containing unicellular algae one day after layering the cell sheets revealed values of 1.84 and 1.70, respectively (Table 2). On the other hand, L/G ratios of the 5-layered and 10-layered cardiac cell sheets one day after layering with unicellular algae revealed values of 1.52 and 1.41, respectively (Table 2). This suggests that a portion of the cardiac cells switched from anaerobic respiration to aerobic respiration due to the presence of oxygen produced by the unicellular algae. 38 moles of ATP are produced from 1 mole of glucose during aerobic respiration. On the other hand, 2 moles of ATP are produced from 1 mole of glucose during anaerobic respiration. Consequently, there is the possibility of a correlation between the reductions in glucose consumption and lactate production attributable to co-cultivation of rat cardiac cells and unicellular algae and efficient energy production by aerobic respiration.

There were hardly any significant changes observed in L/G ratios during co-cultivation of unicellular algae and C2C12 cell sheets or during co-cultivation of unicellular algae and monolayer cardiac cell sheets (Table 2). On the other hand, glucose consumption and lactate production decreased as a result of co-cultivating with unicellular algae (FIG. 6). Thus, there is the possibility that changes in L/G ratio attributable to the supply of oxygen are dependent on cell type. Some types of body tissue and cells are able to survive under anaerobic conditions, and these tissues and cells are thought to produce lactate from glucose. Skeletal muscle has a smaller number of mitochondria in comparison with other tissue, and is thought to demonstrate a high level of tolerance to hypoxic conditions.

Figure 9:
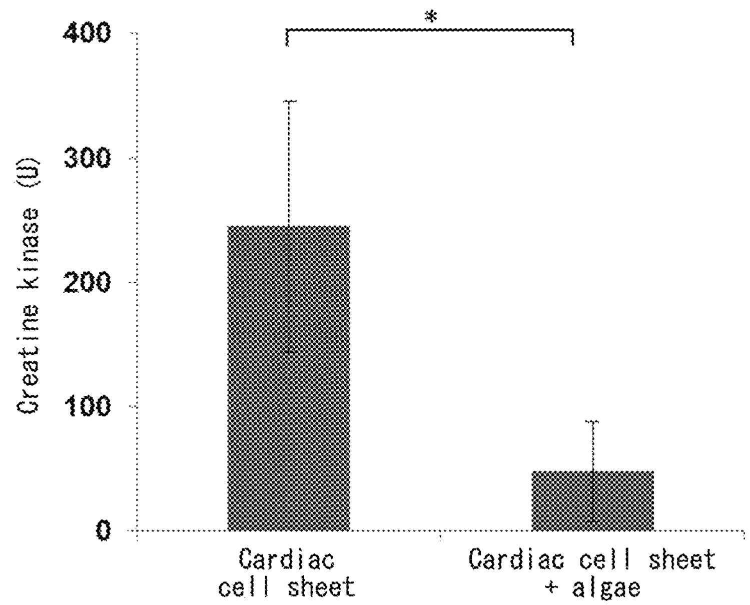
FIG. 9 is a graph indicating the amounts of creatine kinase released (units: U) by a ten-layered cardiomyocyte sheet in the presence or absence of *Chlorococcum littorale.*
Figure 10:
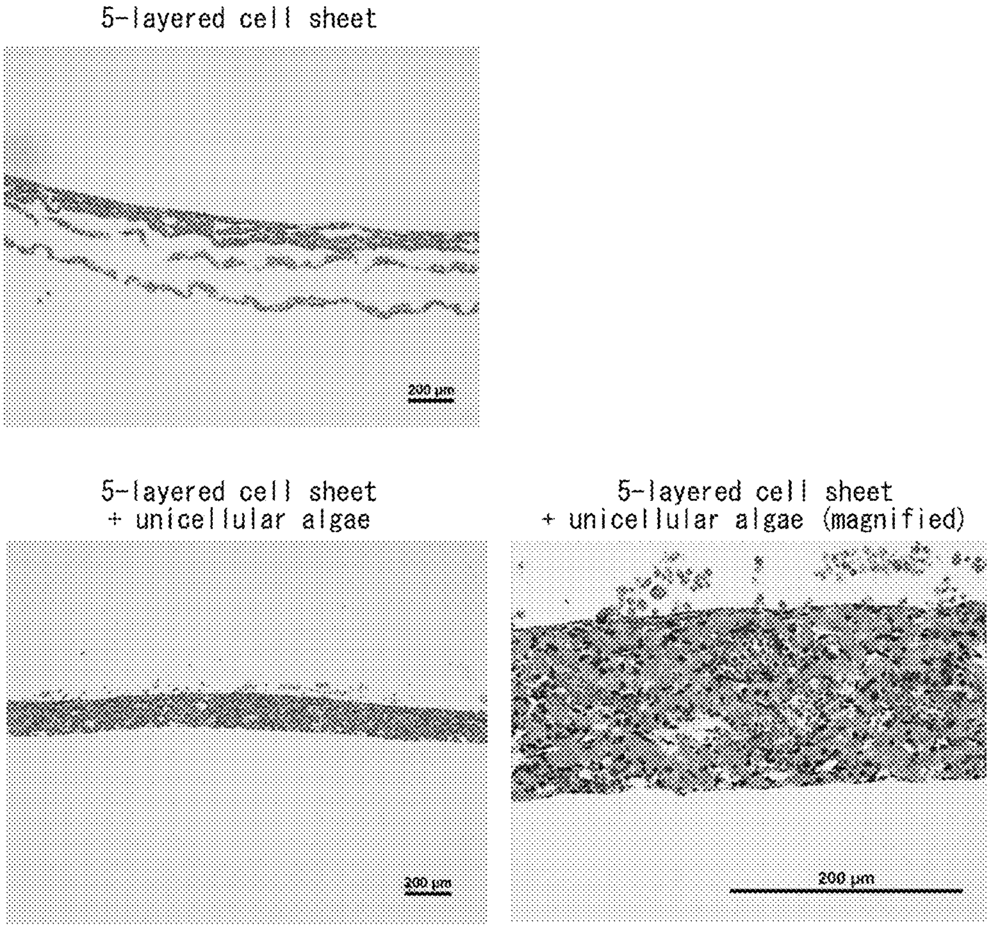
FIG. 10 depicts photomicrographs showing the results of histological observation of a five-layered cardiomyocyte sheet in the presence or absence of *Chlorococcum littorale.*
Figure 11:
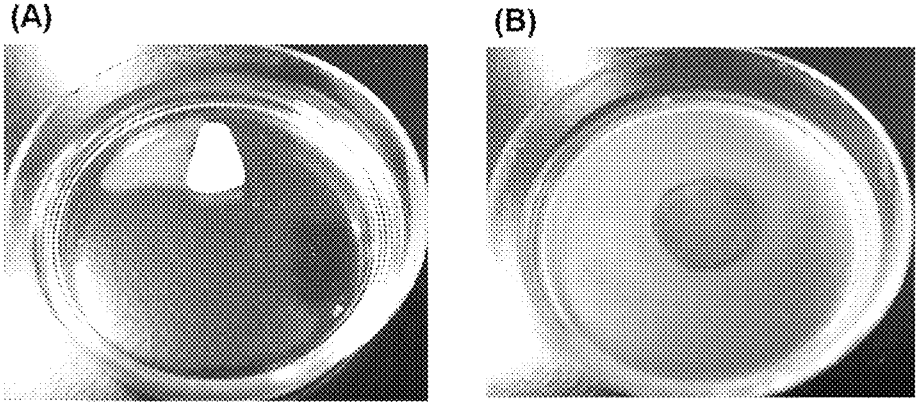
FIG. 11 depicts photographs showing a ten-layered cardiomyocyte sheet in the absence (A) or presence (B) of *Chlorococcum littorale.*

The 10-layered rat cardiac cell sheets released a large amount of CK, indicating considerable damage to cardiomyocytes (FIG. 9). On the other hand, the amount of CK released by the 10-layered cardiac cell sheets co-cultivated with unicellular algae decreased to one-fifth that amount, thereby clearly demonstrating alleviation of cell damage (FIG. 9). Among the 5-layered cardiac cell sheets, the cell sheets close to the culture dish underwent interlayer detachment resulting in cell damage (FIG. 10). On the other hand, the 5-layered cell sheets co-cultivated with unicellular algae were observed to survive even when layered. The 10-layered cardiac cell sheets not containing unicellular algae ended up detaching from the culture dish within 6 days after culturing and were subjected to considerable damage (FIG. 11A). However, the 10-layered sheets co-cultivated with unicellular algae and having unicellular algae interposed between each layer remained adhered to the culture dish without becoming detached and survived even after culturing for 6 days (n=5) (FIG. 11B).

Example 4

(Effect of Co-Cultivation with Unicellular Algae on Ammonia Production)

Figure 12:
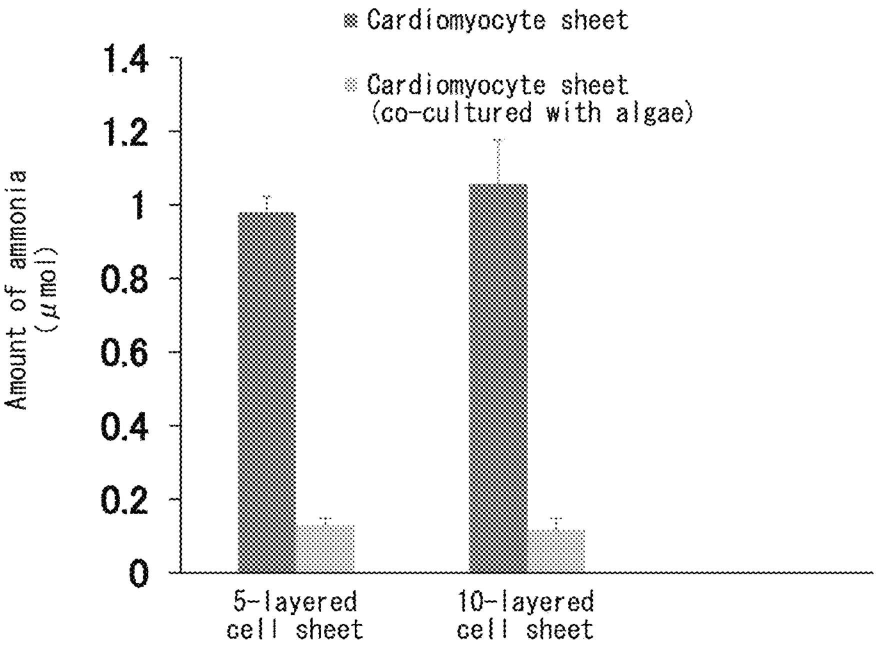
FIG. 12 is a graph indicating the amount of ammonia produced (units: μmol) by a five-layered or ten-layered cardiomyocyte sheet in the presence (co-cultivation) or absence of *Chlorococcum littorale.*

When animal cells are cultured, ammonia is released into the culture medium due to the metabolic activity thereof. This increase in ammonia concentration impairs the growth of animal cells. Ammonia concentrations in the culture medium were measured in order to investigate the effect of co-cultivation with unicellular algae on increases in the concentration of ammonia released from cardiac cell sheets. As a result, ammonia concentrations in the culture medium decreased significantly as a result of co-cultivating with unicellular algae for both 5-layered and 10-layered cell sheets, thereby demonstrating an improvement in the culture environment of the animal cells (FIG. 12).

Example 5

(Effect of Co-Cultivation with Unicellular Algae on Elimination of Hypoxic State)

Figure 13:
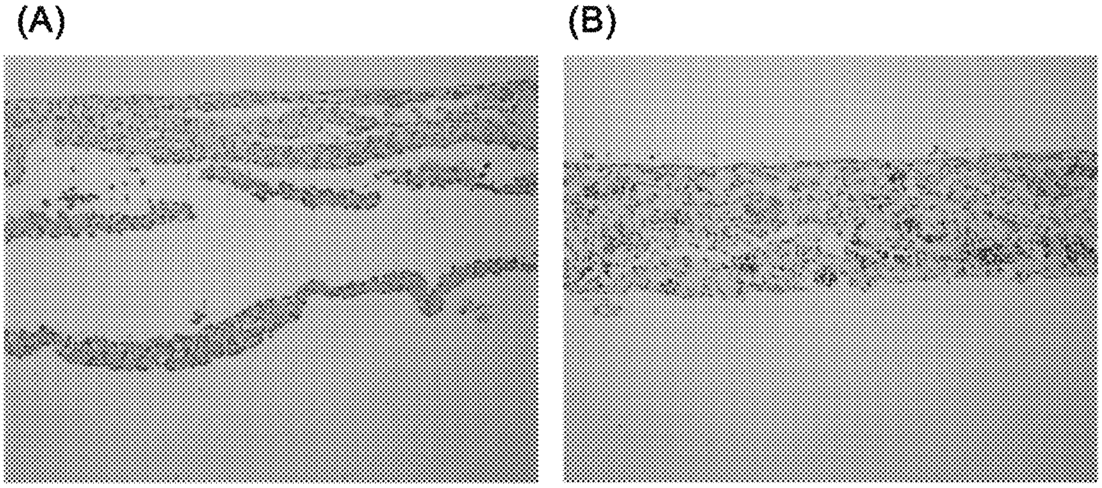
FIG. 13 depicts photomicrographs of the results of histological observation of a five-layered cardiomyocyte sheet in the presence (co-cultivation) or absence of *Chlorococcum littorale*. HIF-1α-positive cells were stained using anti-HIF-1α antibody. Results for the five-layered cardiomyocyte sheet only are shown in FIG. 13(A), while results for the five-layered cardiomyocyte sheet in the presence of *Chlorococcum littorale* (co-cultivation) are shown in FIG. 13(B).

As the number of layers of a cell sheet increases, those sites of the layered cell sheet farthest from the surface of the cell culture medium fall into a state of insufficient oxygen resulting in cell death. When cells become hypoxic in this manner, a hypoxia-inducible factor in the form of HIF-1$\alpha$ protein is detected. Consequently, a hypoxic state within a tissue can be determined by investigating the presence or absence of expression of this HIF-1$\alpha$ protein. Therefore, immunohistological observations were carried out using anti-HIF-1$\alpha$ antibody in order to determine the effect of the presence or absence of unicellular algae on the hypoxic state of 5-layered cell sheets (FIG. 13). As a result, in the case of culturing a 5-layered cell sheet without using unicellular algae, the lower cell layers were positive for HIF-1$\alpha$ and the tissue was at risk as a result thereof (FIG. 13A). On the other hand, the 5-layered cell sheet co-cultivated with unicellular algae demonstrated few sites stained with anti-HIF-1$\alpha$ antibody, and hypoxia in the lower cell layers was confirmed to have been improved (FIG. 13B).

Example 6

(Culturing of Unicellular Algae Using Culture Medium for Animal Cells)

Algae other than the aforementioned unicellular algae, *Chlorococcum littorale*, were also confirmed to be able to be cultured in culture medium for animal cells. *Acaryochloris marina* was able to be cultured under the same conditions as *Chlorococcum littorale* and was able to be used in applications of the present invention. Moreover, *Stichococcus sp.* and filamentous ulvophytes were able to be cultured at 37° C. using animal cell culture medium (DMEM), and were able to be used in applications of the present invention.

INDUSTRIAL APPLICABILITY

According to the production method indicated in the present invention, a thicker cell composition can be easily prepared. This type of thicker cell composition is useful in regenerative medicine for various tissues and organs, while at the same time being useful as a model for evaluating the efficacy of drugs used for the purpose of providing treatment.

The invention claimed is:

1. An in vitro method for culturing an animal cell composition composed of four or more animal cell layers, the method comprising:

(i) sandwiching unicellular algae between each of the animal cell layers so that the unicellular algae is directly contacted with each of the animal cell layers, to thereby prepare a multi-layered animal cell sheet comprising the unicellular algae and the animal cell layers; and (ii) culturing the multi-layered animal cell sheet in a cell culture medium in the presence of unicellular algae and under exposure to light.

2. The method according to claim 1, wherein the unicellular algae include green algae, unicellular blue-green algae, unicellular red algae, unicellular axle algae and/or unicellular algae of the class Ulvophyceae.

3. The method according to claim 1, wherein the unicellular algae include *Chlorococcum littorale, Acaryochloris marina, Cyanidium caldarium, Galdieria partita, Stichococcus sp.* and/or filamentous ulvophytes.

4. The method according to claim 1, wherein the animal cell composition contains mammalian cells.

5. The method according to claim 1, wherein the animal cell composition contains cardiomyocytes or myoblasts.

6. The method according to claim 1, wherein the cell culture medium is culture medium for culturing mammalian cells.

7. The method according to claim 1, wherein each of the animal cell layers is obtained by culturing animal cells in a cell culture vessel coated with a polymer for which the molecular structure thereof changes due to stimulation, and then detaching the animal cells in the form of a sheet from the surface of the cell culture vessel by applying the stimulation to the cell culture vessel.

8. The method according to claim 7, wherein the cell culture vessel is a temperature-responsive culture vessel.

* * * * *